United States Patent
Malinak et al.

(10) Patent No.: US 10,544,089 B2
(45) Date of Patent: Jan. 28, 2020

(54) INNOVATIVE PREPARATION AND CRYSTALLIZATION OF IOSIMENOL

(71) Applicant: OTSUKA PHARMACEUTICAL CO., LTD., Tokyo (JP)

(72) Inventors: Jiri Malinak, Jesenice (CZ); Ivan Hlavacek, Prague (CZ); Jiri Prokop, Prague (CZ); Yoshito Masuda, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/772,710

(22) PCT Filed: Nov. 2, 2016

(86) PCT No.: PCT/JP2016/004798
§ 371 (c)(1),
(2) Date: May 1, 2018

(87) PCT Pub. No.: WO2017/077710
PCT Pub. Date: May 11, 2017

(65) Prior Publication Data
US 2019/0177266 A1 Jun. 13, 2019

Related U.S. Application Data

(60) Provisional application No. 62/250,720, filed on Nov. 4, 2015.

(51) Int. Cl.
*C07C 231/12* (2006.01)
*C07C 237/46* (2006.01)
*C07C 231/08* (2006.01)
*B01D 9/00* (2006.01)

(52) U.S. Cl.
CPC ............ *C07C 231/12* (2013.01); *B01D 9/005* (2013.01); *B01D 9/0081* (2013.01); *C07C 231/08* (2013.01); *C07C 237/46* (2013.01); *B01D 2009/0086* (2013.01); *C07B 2200/13* (2013.01)

(58) Field of Classification Search
CPC ............................. C07C 231/08; C07C 237/46
See application file for complete search history.

(56) References Cited

U.S. PATENT DOCUMENTS 5,698,739 A 12/1997 Sovak
2010/0280270 A1* 11/2010 Bailey ................... C07C 231/02
564/153

FOREIGN PATENT DOCUMENTS

WO 2009091758 A1 7/2009

OTHER PUBLICATIONS

International Search Report and Written Opinion issued in PCT/JP2016/004798, dated Jan. 19, 2017, total 10 pages.

* cited by examiner

*Primary Examiner* — Ana Z Muresan
(74) *Attorney, Agent, or Firm* — Hamre, Schumann, Mueller & Larson, P.C.

(57) ABSTRACT

The present invention generally relates to a process of preparing iosimenol and a process of preparing a crystal of iosimenol, as well as a crystal of iosimenol prepared by these processes.

18 Claims, 6 Drawing Sheets

INNOVATIVE PREPARATION AND CRYSTALLIZATION OF IOSIMENOL

TECHNICAL FIELD

The present invention generally relates to a crystal of iosimenol and a process of preparing the crystal. In more detail, the present invention relates to a process of preparing iosimenol and a process of preparing a crystal of iosimenol, as well as a crystal of iosimenol prepared by these processes.

BACKGROUND ART

Iosimenol, N,N'-bis[3-carbamoyl-5-(2,3-dihydroxypropyl-carbamoyl)-2,4,6-triiodophenyl]-N,N'-bis(2,3-dihydroxypropyl)-malonamide, having the structure showed below, has been proposed as a useful nonionic X-ray contrast agent by Dr. Milos Sovak in 1995 (Patent Literature 1).

[Chem. 1]

In order to make iosimenol fit for commercial use as an X-ray contrast agent, it is necessary to manufacture iosimenol in a high yield and then purify the product effectively. Furthermore, an X-ray contrast agent is generally given to a human body in high dose, thus iosimenol as an X-ray contrast agent is specifically required to be in a high purity. However, it has been difficult to purify such a large amount of iosimenol effectively because iosimenol has chiral centers and pseudoasymmetric carbon atom in the bridge and chiral axes.

Patent Literature 2 discloses some synthetic processes of iosimenol. In Patent Literature 2 (Example 9), iosimenol was prepared by reacting 5,5'-[(1,3-dioxo-1,3-propanediyl)diimino]bis[N-(2,3-dihydroxypropyl)-2,4,6-triiodo-1,3-benzenedicarboxamide] (hereinafter, referred to as "CVI") with 3-chloro-1,2-propanediol in water, but the yield was low and the purity of the product was low.

Further, the crude iosimenol was purified through the following steps: deionization, ion-exchange resin adsorption, charcoaling finished by purification using LC reverse phase chromatography (Example 10). The average achieved HPLC purity was around 95% when starting from 85% deionized crude iosimenol.

[Chem. 2]

Iosimenol

Patent Literature 1 also discloses a process of preparing iosimenol as shown below. In the process, CVI was protected with isopropylidene beforehand, and then the protected CVI (CVI diacetonide) was reacted with 3-chloro-1, 2-propanediol in methanol. The present inventors actually reviewed the process, but both of the yield and the purity were low.

efficient method to reach purity requirements. On the other hand, the HPLC methods have many disadvantages such as low yield, extremely high amount of aqueous waste containing organic solvents (1,000 kg per kg of purified material), and enormously high investment costs. Combination of all these disadvantages constitutes outstandingly high production costs.

[Chem. 3]

As mentioned above, it is important to manufacture iosimenol in a high purity for a commercial purpose, thus it is necessary to purify a crude product of iosimenol in some way. For manufacturing process, however, there are some real limitations to purify iosimenol using HPLC. It is evident, that the HPLC method represents a powerful and Crystallization is one of conventional methods for purification of an active pharmaceutical ingredient (API) of contrast media (CM). Although this method is applied on many ionic CM without difficulties for both monomers and dimers, its application on nonionic CM is not so easy and usually requires very specific conditions. Indeed in Patent Literature 1 and Patent Literature 2, there are no descriptions of any crystals of iosimenol.

It is known that some nonionic CM exist in various isomeric forms and large number of these isomers coexists in obtained solid phase.

Specifically, iosimenol provides three types of stereoisomers:

(A) diastereomers and enantiomers from chiral carbon atoms in the side chains or pseudoasymmetric carbon atom in the bridge and chiral axes;

(B) torsion diastereomers (rotamers) as exo/endo isomerism, cis/trans isomerism, syn/anti isomerism and chiral axes;

(C) conformers.

The present inventors applied crystallization methods described in literature, but this approach always failed, independently on using crude or purified iosimenol. If any solid was obtained, we usually obtained solid of gummy consistency and we never observed any purity increase. Also, iosimenol unlike other contrast agent iodixanol or iohexol is practically insoluble in such solvents as alcohols, ethers and alkoxyalcohols. Usual approach like evaporative crystallization or cooling crystallization failed due to either already-mentioned insolubility of iosimenol in selected solvents or extremely high solubility in aprotic solvents like dimethylformamide.

CITATION LIST

Patent Literature

[PL 1] U.S. Pat. No. 5,698,739 B
[PL 2] WO 2009/091758

SUMMARY OF INVENTION

Technical Problem

The main purpose of the present invention is to provide an effective preparation and/or purification of iosimenol in a high yield and in a high purity. With regard to the purification, the principle idea of the invention is a conversion of many present isomers in iosimenol solution to only those isomers that are significantly less soluble in given solvent and crystallize out from solution.

Solution to Problem

The present inventors have intensively studied to carry out the above purpose and then found specific conditions of the process of preparing iosimenol from CVI in a high yield and in a high purity, as well as specific conditions of the crystallization for purification in a high purity. In more detail, the present inventors have found that iosimenol can be prepared from CVI by reacting with an alkylating agent introducing 2,3-dihydroxypropyl group in a high yield and in a high purity in the presence of an inorganic base and a metal halide in a solvent comprising 2-methoxyethanol, and the obtained iosimenol can be further crystallized in a high purity by adjusting solvents and temperature suitably. Based upon the new findings, the present inventors have completed an innovative sequence of procedure which has sufficient purification capacity and reasonable yield, enabling to use the procedure on industrial scale.

The present invention provides crystals and processes to prepare them as shown in the following Term 1 to Term 38.

Term 1. Iosimenol of formula:

[Chem. 4]

prepared by reacting CVI of formula:

[Chem. 5]

with an alkylating agent introducing 2,3-dihydroxypropyl group in the presence of an inorganic base in a solvent comprising 2-methoxyethanol.

Term 2. The iosimenol of Term 1, wherein the alkylating agent introducing 2,3-dihydroxypropyl group is selected from the group consisting of 3-halo-1,2-propanediol (e.g., 3-chloro-1,2-propanediol or 3-bromo-1,2-propanediol; preferably, 3-chloro-1,2-propanediol), and glycidol. The 3-halo-1,2-propanediol also includes protected 3-halo-1,2-propanediol.

Term 3. The iosimenol of Term 1 or 2, wherein the inorganic base is selected from the group consisting of an alkali metal hydroxide and an alkaline earth metal hydroxide.

Term 4. The iosimenol of any one of Terms of 1 to 3, wherein the inorganic base is lithium hydroxide, calcium hydroxide, sodium hydroxide, potassium hydroxide or mixture thereof.

Term 5. The iosimenol of any one of Terms 1 to 4, wherein the reaction to prepare iosimenol is done in the presence of a metal halide besides an inorganic base.

Term 6. The iosimenol of Term 5, wherein the metal halide is $CaCl_2$, $ZnCl_2$, or $MgCl_2$ (preferably, $CaCl_2$).

Term 7. The iosimenol of any one of Terms 1 to 6, wherein the prepared iosimenol is further purified by the crystallization comprising:
Step 1: suspending the deionized iosimenol in a solvent mixture comprising one or more organic solvents and water,
Step 2: subjecting the mixture to heat and/or ultrasonic to make the mixture completely dissolved,
Step 3: continuing to subject the solution to the same or different heat and/or ultrasonic to obtain a crystal, and
Step 4: collecting the resulting crystal on a filter.

Term 8. The iosimenol of Term 7, wherein the heating in Step 2 and/or Step 3 is done with microwave.

Term 9. The iosimenol of Term 7 or 8, wherein the organic solvent in Step 1 comprises one or more $C_1$-$C_6$ linear or branched alkanols, alkoxyalkanols, or $C_2$-$C_8$ aliphatic or $C_4$-$C_6$ cyclic ethers (e.g., cyclopentyl methyl ether, di-t-butyl ether, diethyl ether, diglyme, diisopropyl ether, dimethoxyethane, dimethoxymethane, 1,4-dioxane, ethyl t-butyl ether, methoxyethane, methyl t-butyl ether, 2-methyltetrahydrofuran, morpholine, tetrahydrofuran, tetrahydropyran, and combinations thereof).

Term 10. The iosimenol of Term 7 or 8, wherein the organic solvent in Step 1 is selected from the group consisting of methanol, ethanol, n-propanol, 2-propanol, n-butanol, i-butanol, sec-butanol, tert-butanol, pentanols including isoamylalcohols, hexanols and 2-methoxyethanol, 2-ethoxyethanol, 1-methoxy-2-propanol and 2-isopropoxyethanol.

Term 11. The iosimenol of any one of Terms 7 to 10, wherein the solvent mixture in Step 1 contains up to 20% water.

Term 12. The iosimenol of any one of Terms 7 to 11, wherein the crystallization process in Step 3 may be initiated by adding a seed of iosimenol crystal while or after the temperature is raised.

Term 13. The iosimenol of any one of Terms 7 to 12, wherein trometamol is used to buffer pH during crystallization process.

Term 14. The iosimenol of any one of Terms 7 to 13, wherein Steps 2 and 3 are done at 70° C.-140° C.

Term 15. The iosimenol of any one of Terms 7 to 14, wherein the concentration of iosimenol as the starting material in Step 1 is 10 w/v %-60 w/v %.

Term 16. A crystal of iosimenol characterized by a powder x-ray diffraction pattern having four or more $2\theta \pm 0.2$ peaks and selected from about 8.1°, 9.6°, 9.9°, 10.0°, 10.7°, 15.4°, 16.9°, 18.0°, 18.6°, 18.9°, 20.1°, 20.4°, 21.9°, 22.2°, 22.5°, 24.8°, 26.1°, 26.8°, 27.5°, 28.9°, 29.4°, 29.7°, 30.5°, 34.1° and 34.6°, wherein measurement of said crystal is at a temperature of about 293 K.

Term 17. The crystal of iosimenol of Term 16 characterized by a powder x-ray diffraction pattern having four or more $2\theta \pm 0.2$ peaks and selected from about 8.1°, 20.4°, 21.9°, 22.2°, 22.5°, 26.8° and 30.5°, wherein measurement of said crystal is at a temperature of about 293 K.

Term 18. A crystal of iosimenol characterized by unit cell parameters at T=293K substantially equal to the following: a=21.8919(16) Å, b=9.8210(9) Å, c=20.0233(12) Å, $\alpha$=90°, $\beta$=94.955(1°), $\gamma$=90°, volume 4289(6) Å$^3$ and a monoclinic P21/a space group.

Term 19. The crystal of iosimenol of any one of Terms 16 to 18, wherein the iosimenol is derived from any one of Terms 1 to 15.

Term 20. A process for preparing iosimenol of formula:

[Chem. 6]

comprising reacting CVI of formula:

[Chem. 7]

with an alkylating agent introducing 2,3-dihydroxypropyl group in the presence of an inorganic base in a solvent comprising 2-methoxyethanol.

Term 21. The process of Term 20, wherein the alkylating agent introducing 2,3-dihydroxypropyl group is selected from the group consisting of 3-halo-1,2-propanediol (e.g., 3-chloro-1,2-propanediol or 3-bromo-1,2-propanediol; preferably, 3-chloro-1,2-propanediol), and glycidol.

Term 22. The process of Term 20 or 21, wherein the inorganic base is selected from the group consisting of an alkali metal hydroxide and an alkaline earth metal hydroxide.

Term 23. The process of any one of Terms 20 to 22, wherein the inorganic base is lithium hydroxide, calcium hydroxide, sodium hydroxide, potassium hydroxide or mixture thereof.

Term 24. The process of any one of Terms 20 to 23, wherein the reaction to prepare iosimenol is done in the presence of a metal halide besides an inorganic base.

Term 25. The process of Term 24, wherein the metal halide is $CaCl_2$, $ZnCl_2$, or $MgCl_2$ (preferably, $CaCl_2$).

Term 26. A process for preparation of crystalline iosimenol from saturated or supersaturated solution of said compound comprising:
Step 1: suspending the deionized iosimenol in a solvent mixture comprising one or more organic solvents and water,
Step 2: subjecting the mixture to heat and/or ultrasonic to make the mixture completely dissolved,
Step 3: continuing to subject the solution to the same or different heat and/or ultrasonic to deposit a crystal, and
Step 4: collecting the resulting crystal on a filter.

Term 27. The process of Term 26, wherein the heating in Step 2 and/or Step 3 is done with microwave.

Term 28. The process of Term 26 or 27, wherein the organic solvent in Step 1 comprises one or more $C_1$-$C_6$ linear or branched alkanols, alkoxyalkanols, or $C_2$-$C_8$ aliphatic or $C_4$-$C_6$ cyclic ethers (e.g., cyclopentyl methyl ether, di-t-butyl ether, diethyl ether, diglyme, diisopropyl ether, dimethoxyethane, dimethoxymethane, 1,4-dioxane, ethyl t-butyl ether, methoxyethane, methyl t-butyl ether, 2-methyltetrahydrofuran, morpholine, tetrahydrofuran, tetrahydropyran, and combinations thereof).

Term 29. The process of Term 26 or 27, wherein the organic solvent in Step 1 is selected from the group consisting of methanol, ethanol, n-propanol, 2-propanol, n-butanol, i-butanol, sec-butanol, tert-butanol, pentanols including isoamylalcohols, hexanols and 2-methoxyethanol, 2-ethoxyethanol, 1-methoxy-2-propanol and 2-isopropoxyethanol.

Term 30. The process of any one of Terms 26 to 29, wherein the solvent mixture in Step 1 contains up to 20% water.

Term 31. The process of any one of Terms 26 to 30, wherein the crystallization process in Step 3 may be initiated by adding a seed of iosimenol crystal while or after the temperature is raised.

Term 32. The process of any one of Terms 26 to 31, wherein trometamol is used to buffer pH during crystallization process.

Term 33. The process of any one of Terms 26 to 32, wherein Steps 2 and 3 are done at 70° C.-140° C.

Term 34. The process of any one of Terms 26 to 33, wherein the concentration of iosimenol as the starting material in Step 1 is 10 w/v %-60 w/v %.

Term 35. The iosimenol of any one of Terms 1 to 15, wherein the purity of iosimenol is highly pure (more than 97%, preferably more than 99%).

Term 36. The iosimenol of any one of Terms 1 to 15, and 35, wherein the total contents of impurities are less than 3% (preferably, 1%).

Term 37. The crystal of any one of Terms 16 to 19, wherein the purity of iosimenol is highly pure (more than 97%, preferably more than 99%).

Term 38. The crystal of any one of Terms 16 to 19, and 37, wherein the total contents of impurities are less than 3% (preferably, 1%).

The above purity and each content of impurities can be measured by, for example, HPLC area normalization method.

During the process of crystallization, iosimenol rotamers in the solution are converted into a preferred rotamer that is significantly less soluble and crystallizes out of the solution.

Effect of Invention

With respect to a process to prepare iosimenol from CVI and 3-halo-1,2-propanediol or glycidol, iosimenol can be prepared in a high yield and in a high purity by reacting CVI without protection with 3-halo-1,2-propanediol or glycidol in the presence of an inorganic base and metal halide (e.g. $CaCl_2$, $ZnCl_2$, $MgCl_2$) in a solvent comprising 2-methoxyethanol. Furthermore, the obtained iosimenol is deionized and then can be purified by the crystallization in a solvent mixture comprising one or more organic solvents and water with heat and/or ultrasonic. The present invention can make it possible to prepare a highly pure iosimenol.

DESCRIPTION OF EMBODIMENTS

Preparation of Crude Iosimenol

The concentration of CVI in the reaction mixture is 5 to 20 w/w %, preferably 10 to 15 w/w %.

The amount of 3-halo-1,2-propanediol or glycidol is 2.0 to 4.0 moles per one mole of CVI, preferably 3.6 to 3.8 moles.

The inorganic base used in the reaction that iosimenol is prepared from CVI and 3-halo-1,2-propanediol or glycidol includes an alkali metal hydroxide and an alkaline earth metal hydroxide, for example, lithium hydroxide, calcium hydroxide, sodium hydroxide, potassium hydroxide, or mixture thereof.

The amount of the inorganic base is 3.0 to 5.0 moles per one mole of CVI, preferably 4.0 moles.

The metal halide used in the reaction that iosimenol is prepared from CVI and 3-halo-1,2-propanediol or glycidol includes $CaCl_2$, $ZnCl_2$ and $MgCl_2$, preferably $CaCl_2$. The $CaCl_2$ includes $CaCl_2$ $(H_2O)_x$ wherein x=0, 2, 4, and 6, the $ZnCl_2$ includes $ZnCl_2(H_2O)_y$, wherein y=0, 1, 1.5, 2.5, 3 and 4, and the $MgCl_2$ includes $MgCl_2(H_2O)_z$ wherein z=0, 2, 4 and 6.

The amount of the metal is 3.0 to 5.0 moles per one mole of CVI, preferably 4.0 moles.

The solvent used in the reaction that iosimenol is prepared from CVI and 3-halo-1,2-propanediol or glycidol is 2-methoxyethanol or a solvent comprising 2-methoxyethanol. The solvent comprised besides 2-methoxyethanol includes, for example, glycerin, the amount of glycerin is 0.2 to 0.3 grams per one gram of CVI, preferably 0.25 grams. The 2-methoxyethanol is added in an amount of 2.5 to 6 mL per gram of CVI, preferably 3.0 to 3.5 mL.

The reaction temperature when iosimenol is prepared from CVI and 3-halo-1,2-propanediol or glycidol is 20° C. to 80° C., preferably 30° C. to 70° C., more preferably 40° C. to 50° C.

The reaction time when iosimenol is prepared from CVI and 3-halo-1,2-propanediol or glycidol is 10 hours to 70 hours, preferably 16 hours to 48 hours, more preferably 18 hours to 24 hours.

The impurities produced when crude iosimenol is prepared are mainly IMP1, IMP2, IMP3, and IMP4 which are over-alkylated compounds. The structures thereof are presumed as shown below.

[Chem. 8]

Impurity IMP1

[Chem. 9]

Impurity IMP2

[Chem. 10]

Impurity IMP3

[Chem. 11]

Impurity IMP4

Deionization of Crude Iosimenol

Deionized crude iosimenol as the starting material in the crystallizing process can be prepared from crude iosimenol as mentioned below. Obtained crude iosimenol contains inorganic salts and other ionic organic impurities. Aqueous solution of crude iosimenol can be deionized by nanofiltration or by ion-exchange resins.

(1) Deionized crude iosimenol can be solidified by proper conventional methods, e.g. by precipitation of concentrated solution in alcohol or by spray drying. Concentration of the aqueous solution can be made by heat evaporation under reduced pressure or by nanofiltration combined with reverse osmosis.

(2) Also another possibility is a direct use of deionized crude iosimenol as aqueous solution and concentrated via azeotropic distillation with 2-methoxyethanol. Water content is monitored and after water removal by the distillation the ratio of crystallization solvent is adjusted.

The quality of the starting deionized crude iosimenol can affect the purity of crystallized iosimenol, i.e., achieved purity of crystallized material depends on the purity of starting crude deionized iosimenol. Lower quality material (below 92%) requires double crystallization to achieve purity above 98%.

Starting material for crystallization must be deionized and reasonably pure. At the current stage of development, we are able to achieve final purity of iosimenol crystals around 97%, if we apply this method on deionized crude iosimenol API with starting purity 86-90% of HPLC area. To achieve purity over 98%, it can be presumed that the purity of starting material must be over 94%. We assume that this starting purity 94% is achievable, if the synthesis of intermediates according to Patent Literature 1 will be well optimized.

Crystalline Iosimenol

The crystals of iosimenol can be characterized via crystallography techniques, such as (but not limited to) X-ray diffraction, neutron diffraction, electron diffraction, and/or the like. In some embodiments, the iosimenol crystals can be characterized by x-ray diffraction patterns, or by one or more lattice parameters, or combinations thereof, for example as described herein.

The crystal of iosimenol can be characterized by a powder x-ray diffraction pattern having four or more 2θ±0.2 peaks and selected from about 8.1°, 9.6°, 9.9°, 10.0°, 10.7°, 15.4°, 16.9°, 18.0°, 18.6°, 18.9°, 20.1°, 20.4°, 21.9°, 22.2°, 22.5°, 24.8°, 26.1°, 26.8°, 27.5°, 28.9°, 29.4°, 29.7°, 30.5°, 34.1° and 34.6°, wherein measurement of said crystal is at a temperature of about 293 K.

Character of the crystal of iosimenol can be measured with the measurement instruments used in the working examples described below, but should not be limited thereto.

General Procedure of Crystallization

Some conditions of crystallizing procedure are shown below, but should not be limited thereto.

(1. Composition of Solvent Mixture)

Composition of the crystallization solvent mixture is a fundamental parameter of the crystallization. The solvents used in the purification are mainly composed of a mixture of 2-methoxyethanol and water, whose ratio in volume is selected from the range of 98:2 to 80:20. A stoichiometric amount of water is needed in the solvent mixture, but more than 10% water can reduce the yield in the purification. Besides 2-methoxyethanol, other solvents may be used such as one or more $C_1$-$C_6$ linear or branched alkanols, alkoxyalkanols, and $C_2$-$C_8$ aliphatic or $C_4$-$C_6$ cyclic ethers. The alkanols include methanol, ethanol, n-propanol, 2-propanol, n-butanol, i-butanol, sec-butanol, tert-butanol, pentanols including isoamylalcohols, and hexanols; the alkoxyalkanols include 2-methoxyethanol, 2-ethoxyethanol, 1-methoxy-2-propanol, and 2-isopropoxyethanol; and the ethers include cyclopentyl methyl ether, di-t-butyl ether, diethyl ether, diglyme, diisopropyl ether, dimethoxyethane, dimethoxymethane, 1,4-dioxane, ethyl t-butyl ether, methoxyethane, methyl t-butyl ether, 2-methyltetrahydrofuran, morpholine, tetrahydrofuran, and tetrahydropyran.

(2. Providing Energy)

Supply of energy such as heat and ultrasonic, specifically heat, to the crystallization mixture is useful to promote the crystallization in high purity. It is also possible to heat the mixture with microwave energy. Temperature during crystallization process should be above 50° C., preferably 70-140° C., more preferably 80-110° C., ideally 90-100° C. Higher temperature, ultrasonic and microwaves can promote the kinetics of the crystallization process. The most convenient temperature for crystallization is at the boiling point of the used solvent mixture. The pressure applied is atmospheric, or elevated, if required temperature exceeds the boiling point of the solvent mixture at atmospheric pressure. Heat and mass transfer is achieved by stirring or by ultrasound. Seeding of crystallization mixture may be necessary.

(3. Time of Crystallization)

Time of crystallization is not limited as long as a sufficient amount of the crystal is deposited. In general, the time is about 10 to 200 hours, preferably about 20 to 150 hours.

Short time thereof can lead to low yield, whereas long time thereof can increase decomposition products. In order to shorten the time of crystallization, microwave or ultrasonic can assist the crystallization with heat.

(4. Concentration of Iosimenol in Crystallization Solvent)

Concentration of the starting material iosimenol in the solvent mixture for crystallization is 10 to 60 w/v %, preferably 20 to 50 w/v %, more preferably 25 to 40 w/v %.

(5. Seeding)

Seeding of crystallization mixture with small amount of crystalline iosimenol increases yield and purity and dramatically reduces (about 50%) crystallization time. The amount of crystalline iosimenol added for seeding is not limited. To get a rough idea, 0.1 to 10 w/w % per crude iosimenol can be used.

Specific Condition of Innovative Crystallization of Iosimenol

Main parameters having influence on crystallization of iosimenol can be:

composition and pH of crystallization solution
temperature of crystallization process
time of crystallization
presence of intentionally added crystallization centers (seeding)
mixing of solution during crystallization process
concentration of iosimenol in crystallization solution
presence of ionic materials in crude iosimenol
purity of starting crude iosimenol but not all the parameters need to be explicitly defined.

Although contrast media are relatively stable compounds, usually after a long-term exposure to heat, certain degradation may occur. The most vulnerable are amide groups and covalently bound iodine. In case of iosimenol, the acidic hydrogens on aliphatic carbon of malonyl group may cause cleavage of the bridge at higher temperature and can lead to form monomeric impurities. These all mentioned degradations are more intensive under strong acidic or strong basic conditions. Using our experience in formulation of iosimenol, we used trometamol as a buffer to control pH between 6-7 from the viewpoint of influencing of color. Ideal conditions for iosimenol crystallization are when the crystallization is performed at shortest process time at lowest possible temperature under suitable and controlled pH between 6-7 by buffer from the viewpoint of influencing of color.

Through visual observation (change of color solution to slightly yellow-brown), we found that, between 80-110° C., the change of color is not intensive and no new impurities or increased level of known impurities are observed. Therefore, ideal conditions for crystallization are temperatures between 80-110° C., pH 6-7 and as short as possible time for crystallization.

Reduction of time necessary for completion of crystallization was achieved by microwave assisted crystallization or by ultrasound. Both methods significantly reduce time of crystallization.

The concentration of iosimenol in crystallization solvent mixture has a significant influence on yield and purity.

We found that this phenomenon is driven mainly by the ratio between iosimenol and 2-methoxyethanol rather than other cosolvents (water, n-butanol). The optimal ratio is iosimenol/2-methoxyethanol about 40/100. Any significant deviation from this ratio lowers the yield and purity of obtained crystals.

EXAMPLES

Hereinafter, the present invention is illustrated by the following examples, but should not be construed to be limited thereto, and it is possible to vary each condition unless the variation is beyond the range of the present invention.

Example 1. Preparation of Iosimenol (Laboratory Scale)

[Chem. 12]

250 mL three neck round-bottomed flask equipped with a magnetic stirrer was charged with 5,5'-[(1,3-dioxo-1,3-propanediyl)diimino]bis[N-(2,3-dihydroxypropyl)-2,4,6-triiodo-1,3-benzenedicarboxamide] (CVI) (36.0 g, 0.027 mol), methoxyethanol (108 mL), lithium hydroxide monohydrate (4.54 g, 0.110 mol), glycerin (9.0 g) and anhydrous calcium chloride (12.0 g, 0.108 mol). The mixture was heated to 50-55° C. Then, 3-chloro-1,2-propanediol (11.35 g, 0.103 mol) was added thereto, maintaining the internal temperature at 40-45° C. The reaction mixture was heated for 21 hours at 40-45° C. After this time, the reaction was considered complete; the reaction mixture was precipitated by ethanol (220 mL) at 55-60° C. Cooled suspension (at 10-12° C.) was filtered and washed with methanol (150 mL). The crude product with salts contained 36.8 g of iosimenol (92% of theory).

The crude product containing iosimenol and salts was dissolved in water (500 mL) at pH=1.9-2.0 and at temperature of 40-45° C. Acidity of the solution was adjusted with hydrochloric acid (1:2). The solution was after 10 minutes of stirring cooled to 10-15° C. Conductivity of the solution was adjusted by stirring the solution with anion-exchanger resins (Purolite A-400, 100 g) and cation-exchanger resins (Purolite C-100, 48 g). The mixture was stirred for 2 hours at 20-30° C. with adding of 500 mL of water. The mixture with resins (conductivity of 0.8 µS/cm) was filtered and washed with water (100 mL). The filtrate was concentrated on rotary evaporator and dried to solid form. Then solid was transferred to glass drying tray and dried in a vacuum oven at 55-60° C. under nitrogen atmosphere. The obtained crude iosimenol is a white-off deionized powder (27.28 g, 68.2% of theory) with HPLC purity 93.22 area %. Overalkyls: imp. IMP1+IMP2: 2.55%, imp. IMP3: 0.29% and imp. IMP4: 0.56%.

Following the working examples disclosed in Patent Literature 1 (U.S. Pat. No. 5,698,739 B) and Patent Literature 2 (WO 2009/091758), each crude iosimenol was prepared and their characteristics were analyzed. The results are shown in Table 1 along with the result of Example 1.

TABLE 1

| Process | Yield (% th.) | Impurity profile (area %) | | | |
|---|---|---|---|---|---|
| | | Iosimenol | IMP1 + IMP2 | IMP3. | IMP4. |
| U.S. Pat. No. 5,698,739 A | 81.3 | 73.68 | 3.11 | 3.24 | 2.46 |
| U.S. Pat. No. 8,680,334 B2 | 68.8 | 79.75 | 3.55 | 1.83 | 3.18 |
| Example 1 | 92.0 | 93.22 | 2.55 | 0.29 | 0.56 | note:
"Yield" is directed to crude product containing crude iosimenol and salts.

Example 2. Preparation of Iosimenol (Commercial Scale)

250 L glass-lined reactor equipped with a stirrer was charged with CVI (36.0 kg, 27.07 mol), methoxyethanol (108 L), lithium hydroxide monohydrate (4.54 kg, 108.2 mol), glycerin (9.0 kg) and anhydrous calcium chloride (12.0 kg, 108.1 mol). The mixture was heated to 55-60° C. Then, 3-chloro-1,2-propanediol (11.35 kg, 102.7 mol) was added thereto, maintaining the internal temperature at 50-55° C. The reaction mixture was heated for 16 hours at 55-60° C. After this time, the reaction mixture was precipitated by ethanol (220 L) at 50-55° C. Cooled suspension (at 10-15° C.) was centrifuged and washed with ethanol (60 L). The crude product with salts contained 36 kg of iosimenol (90% of theory).

The crude product containing iosimenol and salts was dissolved in water (140 L) at pH=1.5-2.0 and at temperature of 48-52° C. Acidity of the solution was adjusted with hydrochloric acid (1:2). After 10 minutes of stirring, the solution was cooled to 15-20° C. pH of the solution was adjusted with a solution of sodium hydrogen carbonate to pH of 5.2-5.8. Main portion of the salts was removed by using of nanofiltration unit to achieve the conductivity between 0.2-0.7 mS/cm. The target conductivity of the solution was adjusted by stirring the solution with anion-exchanger resin (Purolite A-400, 8-10 kg) and cation-exchanger resin (Purolite C-100, 2-3 kg). The mixture with resins was stirred for 2 hours at 20-30° C. When conductivity 0.3-1.0 µS/cm was achieved, the resins were filtered off and washed with water (20 L). The filtrate was charcoaled two times (2×0.86 kg) for 1 hour at 55-60° C. The cooled filtrate (15-20° C.) was concentrated on reverse osmosis unit to a density 1.40-1.41 g/ml (about 50 w/w %). The concentrated solution of iosimenol was charged into ethanol (300 L) during 1 hour at 55-60° C. The suspension of iosimenol was cooled and the precipitated iosimenol was centrifuged and washed with ethanol. The solid was dried at max. 50° C. for 12 hours. The dried iosimenol was dissolved into 20-30 w/w % aqueous solution and solidified by spray drying.

Yield of iosimenol is 26 kg (65% of theory) with HPLC purity 91.61%. Overalkyls: imp. IMP1+IMP2: 2.75%, imp. IMP3: 0.44% and imp. IMP4: 0.41%.

Preparation of Seed for Crystallization

First crystals of iosimenol were obtained during the initial experiments on crystallization. Amorphous crude iosimenol (75 g) was firstly purified by column chromatography (achieved purity 98.1%) and then crystallized in mixture of 2-methoxyethanol (50 mL) and methanol (7 mL). The crystallization mixture was refluxed for 24 hours. Then the mixture was diluted with a mixture of water and methanol (8 mL and 10 mL, respectively). Then, fraction of solvent (10 mL) was distilled-off during 1 hour. The remaining mixture was maintained for next 24 hours under reflux and then cooled to 65° C. during 5 hours. Then 2-methoxyethanol was added (70 mL) and the obtained mixture was heated to reflux. The first traces of solid appeared after 5 days and prolonging of reflux for further 15 days caused substantial crystallizing of the material. The crystals were separated and used as seeding in future experiments.

Preparation of Crystal of Iosimenol

Three typical processes of crystallization of iosimenol are shown below in three examples.

(1) Crystallization of Iosimenol Using Conventional Heating—Example 3

Nanofiltered, deionized and charcoaled aqueous solution of crude iosimenol (purity 96-97% HPLC area) was concentrated under reduced pressure to dryness. 40 grams (calculated on anhydrous base) of the iosimenol was suspended in solvent mixture containing 2-methoxyethanol (100 mL) water (2.5-7 mL) and n-butanol (5-10 mL) in a 250 mL three-necked flask equipped with a condenser. The suspension was stirred and heated up to 85° C. until clear solution is obtained, then heated to reflux and seeds of iosimenol crystals (0.5-1.0 g) were added. The mixture was maintained under reflux. The first crystals appeared after 6-12 hours. The course of crystallization was checked by monitoring of remaining dissolved iosimenol in sample of liquid phase and when remaining iosimenol stayed unchanged in two consecutive testing, the suspension was filtered at 80-90° C. The obtained solid material was washed with ethanol (100 mL) at 60-70° C. The HPLC purity of the crystals was 98.5-99.2% and the crystallization yield was 50-53%. Total time of the crystallization was 72 hours.

(2) Crystallization of Iosimenol Using Ultrasound—Example 4

Iosimenol and solvent mixture, in ratio and amount as described in previous Example 3, were conventionally heated to reflux and ultrasonicated (20 kHz, pulse mode). Seeds of iosimenol crystals in proportion to deionized crude iosimenol corresponding to Example 3 were added. The mixture was maintained under reflux and ultrasonicated. The course of crystallization was checked in the same way as in Example 3. The suspension of crystalline iosimenol was filtered at 80-90° C. and obtained solid material washed with ethanol at 60-70° C. The HPLC purity of the crystals was 99.1% and the crystallization yield was 45%. Total time of the crystallization was 24 hours.

(3) Crystallization of Iosimenol Using Microwave Irradiation—Example 5

Iosimenol and solvent mixture were prepared and dissolved as described in previous Example 3. The obtained solution was transferred into a flask with crimp top, magnetic stir bar added, seeded with iosimenol crystals in the ratio to crude iosimenol corresponding to Example 3, and tightly closed. Then the stirred solution was irradiated by microwave in Biotage equipment with a preset target temperature 90° C. The obtained suspension of crystalline iosimenol was filtered at 80-90° C. and the solids were washed with ethanol at 60-70° C. The HPLC purity of the crystals was 99.0% and the crystallization yield was 40%. Total time of the crystallization was 16 hours.

Figure 1:
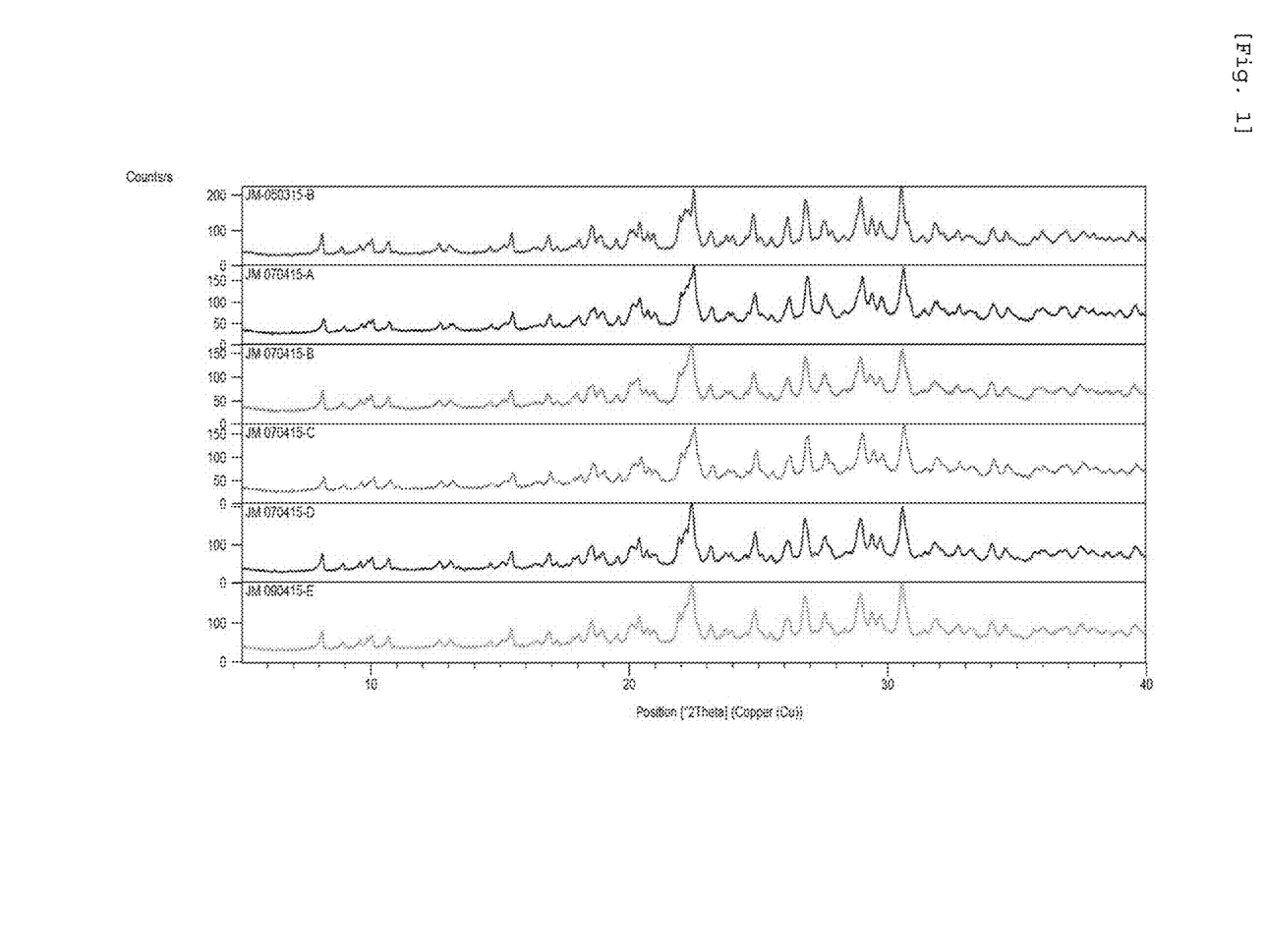
FIG. 1 shows comparison of the powder patterns of samples JM 070415A to JM 070415D, JM-090415E, and JM-050315B.

Powder Diffraction Characterization of Iosimenol Obtained by Innovative Crystallization (1) Source of Sample Used Seven batches of powdered iosimenol were provided, JM-070415A to JM-070415D, JM-090415E, JM-160415 and JM-050315B (see, Table 2). Small amounts of the provided samples were picked for X-ray powder diffraction (XRPD) analysis. Samples JM-070415A to JM-070415D and JM-090415E have got almost the same powder diffraction patterns and are identical with the diffractogram JM-050315B (reference sample). Powder patterns of the samples JM-070415A to JM-070415D and JM-090415E have got the same number of peaks with respect to iosimenol JM-050315B, so they do not contain any other crystalline phase (see, FIG. 1).

TABLE 2

Samples used for XRPD analysis

| Experiment: | JM-050315B* | JM-070415A | JM-070415B | JM-070415C | JM-070415D | JM-090415E | JM-160415** |
|---|---|---|---|---|---|---|---|
| Main purpose of the experiment: | Preparation crystals for crystallographic analysis | | | | | | |
| Starting Iosimenol, purity: | 40 g, 98.75% | 20 g, 98.10% | 20 g, 98.10% | 40 g, 98.10% | 40 g, 98.10% | 40 g, 98.10% | 40 g 98.93% |
| 2-Methoxyethanol: | 100.0 mL | 50.0 mL | 50.0 mL | 100.0 mL | 100.0 mL | 100.0 mL | 100.0 mL |
| n-Butanol: | 5.0 mL | 0.0 mL | 2.5 mL | 0.0 mL | 5.0 mL | 5.0 mL | 10.0 mL |
| Water: | 2.65 mL | 0.0 mL | 0.0 mL | 2.65 mL | 2.65 mL | 2.65 mL | 5.0 mL |
| Trometamol: | no | no | no | no | no | no | no |
| Tested temperature range: | 93-97° C. | 94-99° C. | 94-100° C. | 94-97° C. | 92-97° C. | 95-97° C. | 95-97° C. |
| Seeding: | 0.05 g | no | no | no | no | 2 g | 0.05 g |
| Crystallization observed: | yes | yes | yes | yes | yes | After 38 min. | After 30 min. |
| Time of the crystallization: | 84 hours | 168 hours | 168 hours | 168 hours | 168 hours | 96 hours | 72 hours |
| Water content in crystals by KF: | 0.8% | 1.1% | 0.9% | 1.0% | 0.9% | 1.0% | n.a. |
| Purity of the obtained crystal (% area by HPLC): | 99.03% | 94.31% | 98.64% | 96.93% | 97.77% | 98.47% | 99.13% |
| Yield: | 65.7% | 12.8% | 36.0% | 36.7% | 45.3% | 54.3% | 1.0% |
| Purify of the mother liquor (% area by HPLC) | 96.26% | 84.51% | 96.19% | 88.04% | 90.17% | 90.41% | n.d. |

*Second crystallization (starting material was a crystalline form),
**only this crystallization was without mixing,
n.d. = not detected,
n.a. = not applicable (2) Sample Preparation The samples were examined with an optical microscope and it was found that the size of the crystallite is below 10 micrometers. Unfortunately no suitable single-crystals were observed.

(3) Data Collection

X-ray powder diffraction data were collected at room temperature with an X'Pert PRO 8-8 powder diffractometer with parafocusing Bragg-Brentano geometry using CuK$\alpha$ radiation ($\lambda$=1.5418 Å, U=40 kV, I=30 mA). Data were scanned with an ultrafast detector X'Celerator over the angular range 5-80° (2$\theta$) with a step size of 0.0167° (2$\theta$) and an accumulative counting time 20.32 s·step$^{-1}$. Indexing procedure was performed on more precise data scanned with an accumulative counting time 162.88 s·step$^{-1}$. Data evaluations were performed using the software package HighScore Plus.

(4) References to Programs Used

HighScore Plus, Full Powder Pattern Analysis Software, V3.0e, PANALYTICAL, Almelo, Holland.

Boultif, A. and Luër, D. (2004). "Powder pattern indexing with the dichotomy method", J. Appl. Crystallogr. 37, 724-731.

(5) Results of the Comparison of the Measured Samples

All seven samples have got almost the same X-ray powder patterns. The number of the peaks for all the seven samples in the 2θ range (5-20°, reasonably separated peaks) is the same and the positions of the peaks are the same within the experimental errors. The relative intensities of the peaks are as well almost the same. Therefore we can state that these seven powdered samples have got almost randomly oriented crystallites. See the following Table 3 and diffractograms in FIG. 1.

TABLE 3

PXRD Peak Positions (degrees 2θ ± 0.2)

| JM-070415A | JM-070415B | JM-070415C | JM-070415D | JM-090415E | JM-160415 | JM-050315B |
|---|---|---|---|---|---|---|
| 8.2 | 8.1 | 8.2 | 8.1 | 8.1 | 8.1 | 8.1 |
| 9.6 | 9.6 | 9.6 | 9.6 | 9.6 | 9.6 | 9.6 |
| 9.9 | 9.9 | 9.9 | 9.9 | 9.9 | 9.9 | 9.9 |
| 10.0 | 10.0 | 10.1 | 10.0 | 10.0 | 10.0 | 10.0 |
| 10.7 | 10.6 | 10.7 | 10.7 | 10.7 | 10.7 | 10.7 |
| 15.5 | 15.4 | 15.5 | 15.4 | 15.4 | 15.5 | 15.4 |
| 16.9 | 16.8 | 16.9 | 16.9 | 16.9 | 16.9 | 16.9 |
| 18.0 | 18.0 | 18.1 | 18.0 | 18.0 | 18.1 | 18.0 |
| 18.6 | 18.6 | 18.6 | 18.5 | 18.5 | 18.6 | 18.5 |
| 19.0 | 18.9 | 19.0 | 19.0 | 18.9 | 18.9 | 18.9 |
| 20.1 | 20.1 | 20.1 | 20.1 | 20.0 | 20.0 | 20.0 |
| 20.4 | 20.3 | 20.4 | 20.4 | 20.4 | 20.4 | 20.4 |
| 22.0 | 21.9 | 22.0 | 21.9 | 21.9 | 22.0 | 21.9 |
| 22.2 | 22.1 | 22.2 | 22.2 | 22.2 | 22.2 | 22.1 |
| 22.5 | 22.4 | 22.5 | 22.4 | 22.4 | 22.5 | 22.5 |
| 24.8 | 24.8 | 24.9 | 24.8 | 24.8 | 24.8 | 24.8 |
| 26.2 | 26.1 | 26.2 | 26.1 | 26.1 | 26.2 | 26.1 |
| 26.9 | 26.8 | 26.9 | 26.8 | 26.8 | 26.9 | 26.8 |
| 27.6 | 27.5 | 27.6 | 27.5 | 27.5 | 27.6 | 27.5 |
| 29.0 | 28.9 | 29.0 | 28.9 | 28.9 | 29.0 | 28.9 |
| 29.4 | 29.3 | 29.4 | 29.4 | 29.4 | 29.4 | 29.4 |
| 29.7 | 29.7 | 29.8 | 29.7 | 29.7 | 29.7 | 29.7 |
| 30.6 | 30.5 | 30.6 | 30.5 | 30.5 | 30.5 | 30.5 |
| 34.1 | 34.0 | 34.1 | 34.1 | 34.0 | 34.1 | 34.0 |
| 34.6 | 34.6 | 34.6 | 34.5 | 34.5 | 34.6 | 34.6 |

(6) Results of the Unit Cell Parameters for the Sample Iosimenol JM-050315B

The automatic indexing of results obtained using evaluation software DICVOL04 (reference Boultif, A. and Luër, D. (2004). "Powder pattern indexing with the dichotomy method", J. Appl. Crystallogr. 37, 724-731) has shown, that the compound $C_{31}H_{36}I_6N_6O_{14}$ is monoclinic with space group $P2_1/a$, and the unit-cell parameters were least-square refined to the values:

| a = 21.8919(16) Å, | α = 90° |
|---|---|
| b = 9.8210(9) Å, | β = 94.955(1)° |
| c = 20.0233(12) Å, | γ = 90° |
| Volume | 4289(6) Å³ |

Crystal Class: monoclinic $P2_1/a$
Cell determined from 138 reflections
Cell 2θ range=5-80°
Temperature 293K Evaluation of Particle Morphology, Skeletal and Apparent Density of Crystalline and Sprayed (Amorphous) Iosimenol The objective was to evaluate a solid iosimenol, which was obtained from its solution as a powder form by crystallization, ultrasound assisted crystallization and spray drying. Samples identified as crystallized iosimenol were our main object of interest, while spray-dried iosimenol were studied in order to find the characteristic differences. Each type of iosimenol was represented by one sample.

Particle morphology was evaluated by Scanning Electron Microscopy (SEM) combined with ion microscope FIB-SEM Tescan Lyra3GMU equipped with a number of detectors EDS, EBSD, STEM, EBIC and TOF-SIMS. Due to electric non-conductivity of iosimenol, its molecules accumulate electric charge leading to deterioration of SEM images. Therefore, the samples were coated with a thin layer of platinum for effective removal of electric charges to obtain high quality SEM images.

Skeletal (true) density of the material was measured using helium pycnometer Micomeritics Multivolume Pycnometer 1305 and using mercury porosimeter Micromeritics AutoPore IV.

Apparent (gravity) density, i.e. density covering all open or closed cavities or pores was also measured.

Three samples of iosimenol were analyzed. Results of testing of individual samples obtained from the skeletal density (helium pycnometry and mercury intrusion porosimetry) and apparent density are shown in the Table 4.

TABLE 4

Comparison of skeletal and apparent (true) density of crystalline and spray-dried iosimenol API

| Sample | | $ρ_{He}$ [g cm⁻³] | $ρ_{Hg}$ [g cm⁻³] | $ρ_a$ [g cm⁻³] |
|---|---|---|---|---|
| I-1 | JM-280415; ultrasound, crystallization | 2.3700 | 2.3032 | 1.057 |
| I-2 | PSD 420131115/165; spray-dried | 2.1974 | 1.9837 | 1.193 |
| I-3 | JM-210415TKR; crystallization | 2.4022 | 2.3624 | 1.135 |

$ρ_{He}$ - skeletal density by helium pycnometry,
$ρ_{Hg}$ - skeletal density by mercury porosimetry,
$ρ_a$ - apparent density Slightly lower skeletal density by mercury porosimetry was observed in comparison with skeletal densities by helium pycnometer. These differences are caused by physical properties of the probe used. Smaller and more agile helium is able to explore also cavities that are accessible only through very narrow necks. Based on small difference between densities, we can assume that number of narrow necks (inaccessible for mercury) is very low.

Values of skeletal density indicate significant impairment of spray-dried sample I-2, which can be interpreted as the existence of closed porosity, which occurs quite frequently in spray-dried samples. Closed porosity is also observed in the electron microscope, see in Drawings.

Figure 2:
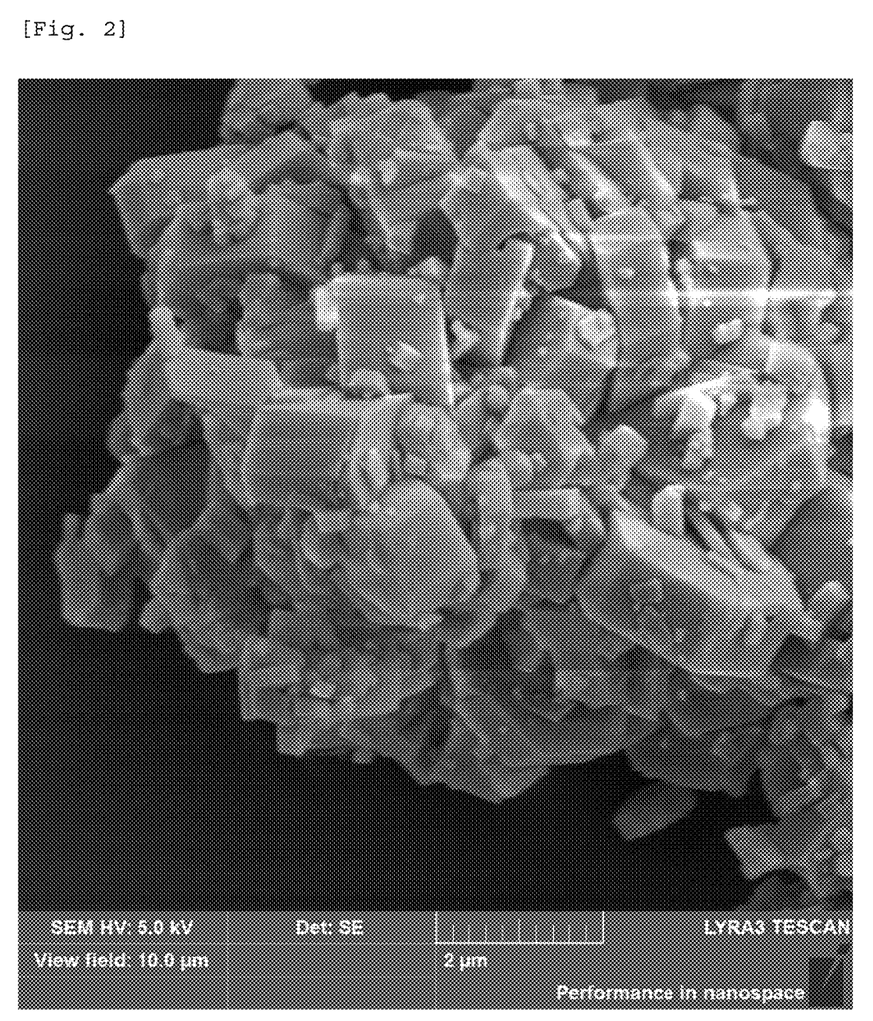
FIG. 2 shows crystalline iosimenol at ultrasound, typical agglomerates consisting of Sample I-1.

Mercury intrusion curve for sample I-1 shows the majority of intrusion volume of mercury in pressure, which can be interpreted as the characteristic size of narrow necks with values of 200 to 300 nm. Such values are consistent with the observed objects in the image of sample I-1 (see, FIG. 2) where hexagonal blocks are clearly visible constituting the agglomerate sample I-1 of approximately 500 to 2,000 nm. Since these numbers are in good agreement with values from the mercury intrusion curve, we can assume that the surface of sample I-1 is formed only by the geometrical shape of non-porous particles.

Figure 3:
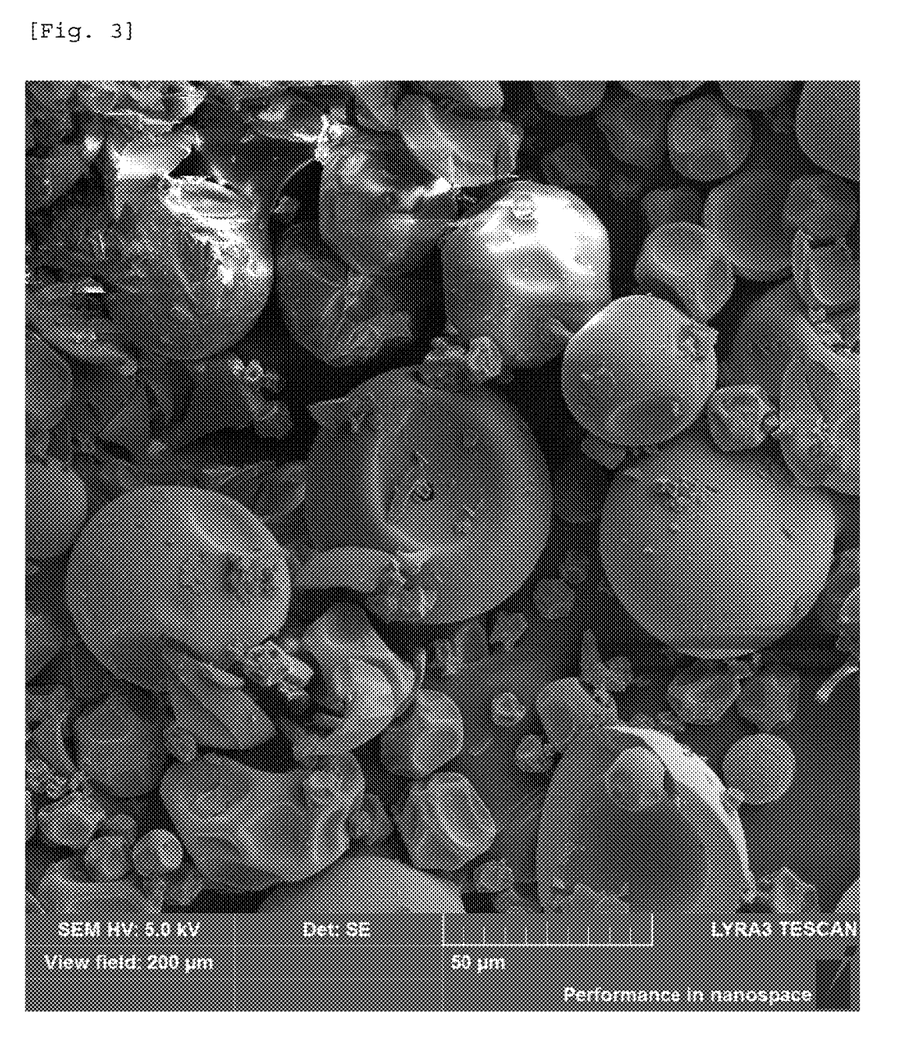
FIG. 3 shows typical spray-dried particles of amorphous iosimenol, Sample I-2.
Figure 4:
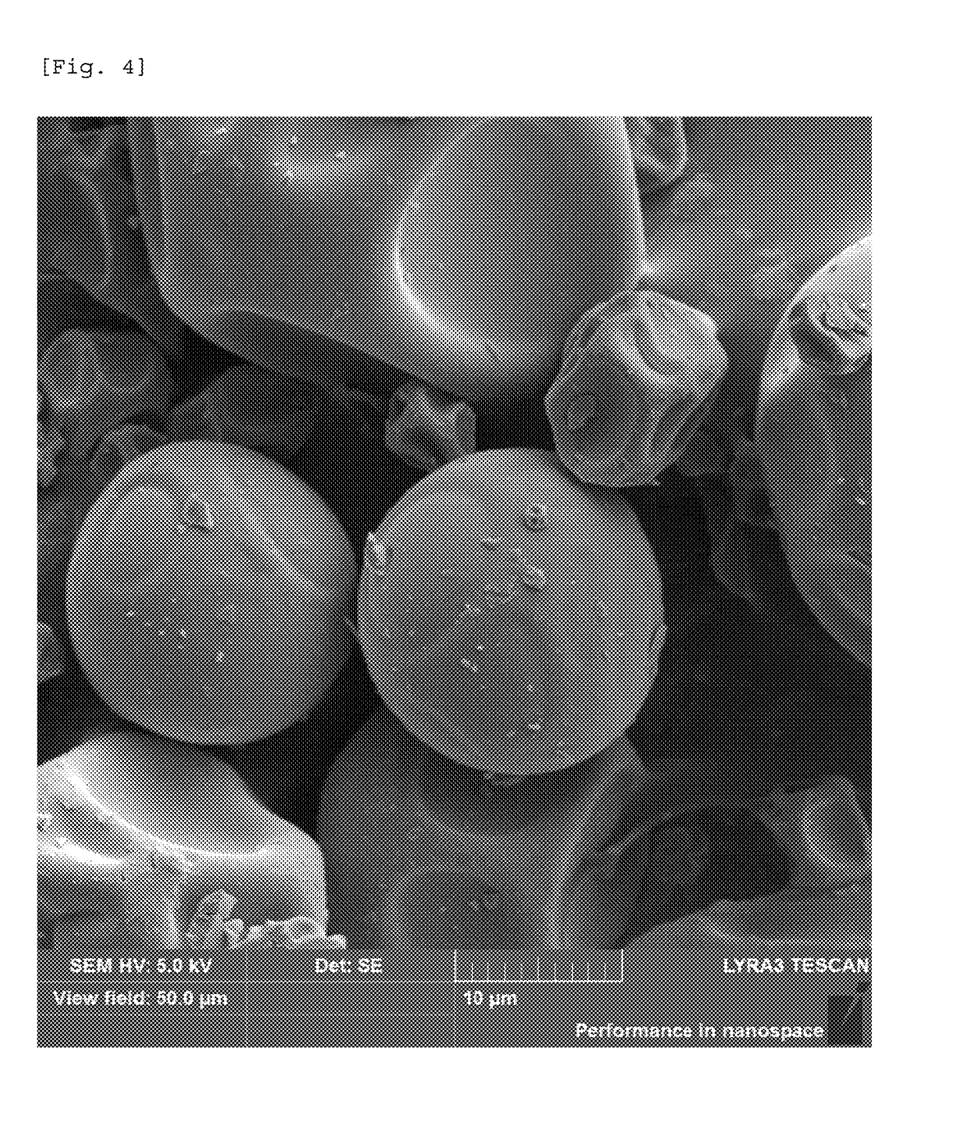
FIG. 4 shows spray-dried amorphous iosimenol, Sample I-2.

Images of sample I-2 (see, FIG. 3 and FIG. 4) reveals two types of spherical particles formed by spray drying. Some are almost smooth, some are slightly deformed. Sample I-2 indicates the presence of a significant quantity of pores with size in the interval of 7-20 nm.

Figure 5:
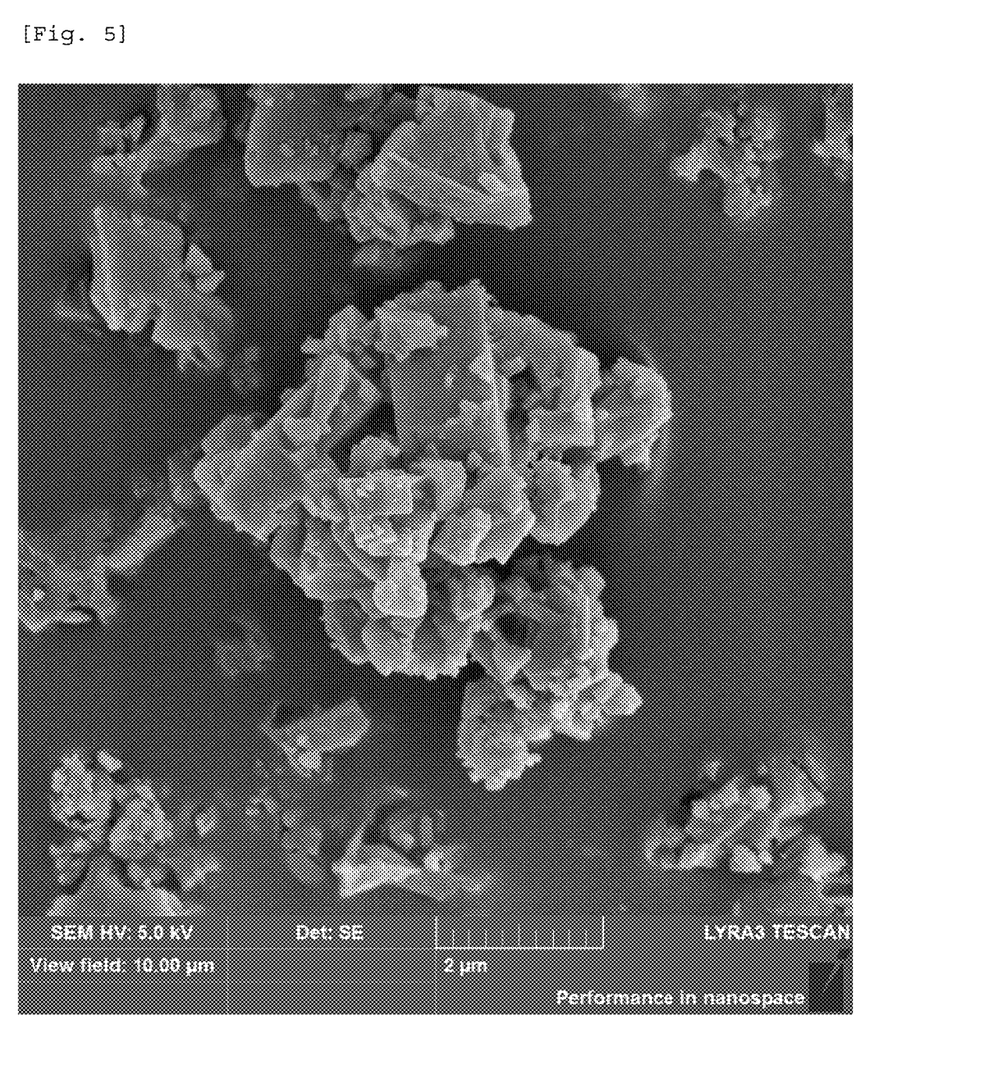
FIG. 5 shows Sample I-3, crystalline iosimenol. Image shows a wide particle size distribution and particle shape diversity.
Figure 6:
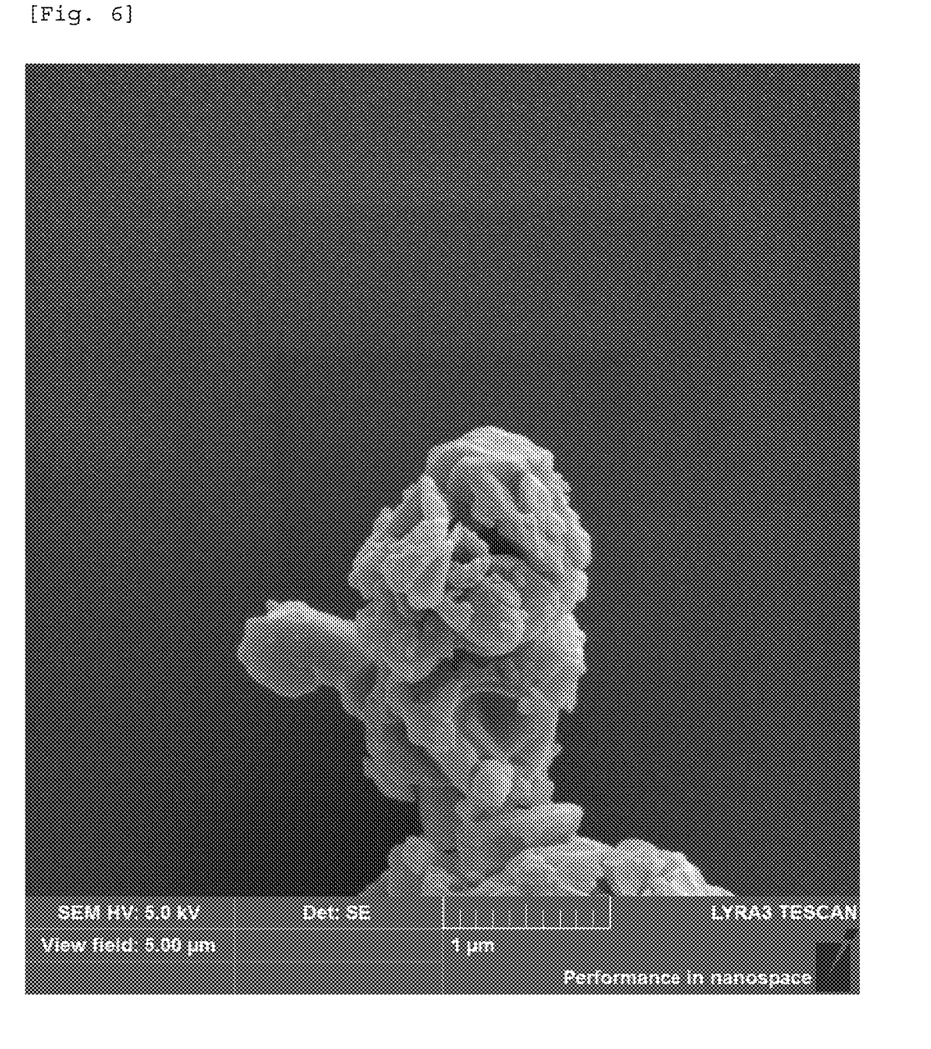
FIG. 6 shows Sample I-3, crystalline iosimenol.

Mercury intrusion curve for sample I-3 shows a gradual filling under of corresponding cylindrical pore with diameter of 100 nm, which can be characterized as narrow necks formed during agglomeration of particles of a sample I-3 (see, FIG. 5, FIG. 6).

Summary of Crystal

XRPD, Scanning Electron Microscopy (SEM) combined with ion microscope FIB-SEM, skeletal density were performed to identify the material obtained by innovative crystallization of deionized crude iosimenol. The obtained results confirmed crystalline structure of iosimenol, uniformity of obtained crystalline phases, i.e. crystals contain only one polymorph.

Crystalline samples of iosimenol, which were prepared by crystallization under various conditions, show identical X-ray powder diffraction. The unit cell of crystals was characterized as monoclinic space group P2$_1$/a, with the following parameters:

| | |
|---|---|
| a = 21.8919(16) Å, | α = 90° |
| b = 9.8210(9) Å, | β = 94.955(1)° |
| c = 20.0233(12) Å, | γ = 90° |

Scanning Electron Microscopy (SEM) combined with ion microscope FIB-SEM provide images of iosimenol solids and those prepared via innovative crystallization shows geometry typical for crystalline phases. Crystals are organized in tetragonal or hexagonal blocks constituting the agglomerates.

INDUSTRIAL APPLICABILITY

The role of invented crystallization is either to fully replace the current HPLC purification technology which is very expensive or to be used in combination with substantially simplified HLPC purification.

The invention claimed is:

1. A crystal of iosimenol characterized by a powder x-ray diffraction pattern having four or more 2θ±0.2 peaks and selected from about 8.1°, 9.6°, 9.9°, 10.0°, 10.7°, 15.4°, 16.9°, 18.0°, 18.6°, 18.9°, 20.1°, 20.4°, 21.9°, 22.2°, 22.5°, 24.8°, 26.1°, 26.8°, 27.5°, 28.9°, 29.4°, 29.7°, 30.5°, 34.1° and 34.6°, wherein measurement of said crystal is at a temperature of about 293 K.

2. The crystal of iosimenol of claim 1 characterized by a powder x-ray diffraction pattern having four or more 2θ±0.2 peaks and selected from about 8.1°, 20.4°, 21.9°, 22.2°, 22.5°, 26.8° and 30.5°, wherein measurement of said crystal is at a temperature of about 293 K.

3. A crystal of iosimenol characterized by unit cell parameters at T=293K substantially equal to the following: a=21.8919(16) Å, b=9.8210(9) Å, c=20.0233(12) Å, α=90°, β=94.955(1)°, γ=90°, volume 4289(6) Å$^3$ and a monoclinic P21/a space group.

4. A process for preparing iosimenol of formula:

[Chem. 3]

comprising reacting CVI of formula:

[Chem. 4]

with an alkylating agent introducing 2,3-dihydroxypropyl group in the presence of an inorganic base in a solvent comprising 2-methoxyethanol.

5. The process of claim 4, wherein the alkylating agent introducing 2,3-dihydroxypropyl group is selected from the group consisting of 3-halo-1,2-propanediol and glycidol.

6. The process of claim 4, wherein the alkylating agent introducing 2,3-dihydroxypropyl group is 3-halo-1,2-propanediol.

7. The process of claim 4, wherein the inorganic base is selected from the group consisting of an alkali metal hydroxide and an alkaline earth metal hydroxide.

8. The process of claim 4, wherein the inorganic base is lithium hydroxide, calcium hydroxide, sodium hydroxide, potassium hydroxide or mixture thereof.

9. The process of claim 4, wherein the reaction to prepare iosimenol is done in the presence of a metal halide besides an inorganic base.

10. The process of claim 9, wherein the metal halide is selected from the group consisting of $CaCl_2$, $ZnCl_2$ and $MgCl_2$.

11. A process for preparation of the crystalline iosimenol of claim 1 from a saturated or supersaturated solution of iosimenol, comprising:
   Step 1: suspending deionized iosimenol in a solvent mixture comprising water and one or more organic solvents selected from the group consisting of $C_1$-$C_6$ linear or branched alkanols, alkoxyalkanols, $C_2$-$C_8$ aliphatic ethers, and $C_4$-$C_6$ cyclic ethers,
   Step 2: subjecting the mixture to heat and/or ultrasonic to completely dissolve the iosimenol in the mixture,
   Step 3: continuing to subject the solution to the same or different heat and/or ultrasonic to deposit the crystalline ioseminol of claim 1, and
   Step 4: collecting the resulting crystalline ioseminol of claim 1 on a filter.

12. The process of claim 11, wherein the heating in Step 2 and/or Step 3 is done with microwave.

13. The process of claim 11, wherein the organic solvent in Step 1 is selected from the group consisting of methanol, ethanol, n-propanol, 2-propanol, n-butanol, butanol, sec-butanol, tert-butanol, pentanols including isoamylalcohols, hexanols and 2-methoxyethanol, 2-ethoxyethanol, 1-methoxy-2-propanol and 2-isopropoxyethanol.

14. The process of claim 11, wherein the solvent mixture in Step 1 contains up to 20% water.

15. The process of claim 11, wherein the crystallization process in Step 3 may be initiated by adding a seed of iosimenol crystal while or after the temperature is raised.

16. The process of claim 11, wherein trometamol is used to buffer pH during crystallization process.

17. The process of claim 11, wherein Steps 2 and 3 are done at 70° C.-140° C.

18. The process of claim 11, wherein the concentration of iosimenol as the starting material in Step 1 is 10 w/v %-60 w/v %.

* * * * *